United States Patent

Steer

[11] Patent Number: 5,302,173
[45] Date of Patent: Apr. 12, 1994

[54] OSTOMY COUPLING

[75] Inventor: Peter L. Steer, Nr East Grinstead, United Kingdom

[73] Assignee: E. R. Squibb & Sons, Inc., Princeton, N.J.

[21] Appl. No.: 868,620

[22] Filed: Apr. 14, 1992

[30] Foreign Application Priority Data

Apr. 18, 1991 [GB] United Kingdom ............... 9108276

[51] Int. Cl.⁵ .............................................. A61F 5/44
[52] U.S. Cl. .................................... 604/338; 604/339; 604/342
[58] Field of Search ........................ 604/277, 338–342; 128/DIG. 24

[56] References Cited

U.S. PATENT DOCUMENTS 4,872,869 10/1989 Johns .................................... 604/339

Primary Examiner—Randall L. Green
Assistant Examiner—Rob Clarke
Attorney, Agent, or Firm—Stuart E. Krieger

[57] ABSTRACT

A coupling for joining a pad or dressing to an ostomy bag including a first member 10 of closed loop form for defining a stoma aperture therein, the first member having a formation which defines two opposed walls, 11, 12, and a second member 20 of closed loop form also defining a stoma aperture. The second member has a projection or wall 21 dimensioned and positioned to fit between and resiliently bear against at least one of the walls when the members are connected in such a way as to make sealing engagement with at least the said one wall. The first member is of channel formation seen in cross section and has an upstanding tapering rib 24 extending from the base of the channel and between its walls. The second member has a tapering groove, of substantially complementary shape to the rib, in that surface of the rib projection or wall 21 which faces towards the first member in the mutually coupled condition of the first and second members.

6 Claims, 3 Drawing Sheets

OSTOMY COUPLING

This invention relates to a coupling for fixing an ostomy bag to a pad or surgical dressing.

Such couplings have been proposed. Examples can be seen in British Patents Nos. 1 571 657 and 2 121 902. It has been found that the comfort in wear and security of attachment of the bag to the pad is seriously affected if it is possible for one coupling part to tilt relative to the other. In this context, "tilt" refers to a twisting possibly with partial deformation of a channel-shaped coupling member so that its planar surface, to which a medical grade adhesive pad is normally attached, lies substantially out of a plane located perpendicular to the axis of the coupling. It will be understood that an ostomy coupling normally has a circular stomal orifice, and the axis referred to is a line normal to the plane of that orifice and passing through the centre of the orifice. Such a tilt might be caused in use, for example, because the weight of the bag contents applies a force transverse to the coupling axis.

The aim of the present invention is to provide an ostomy coupling in which the possibility of tilt is eliminated or greatly reduced.

According to the present invention, there is provided a coupling for joining a pad or dressing to an ostomy bag including a first member of closed loop form for defining a stoma aperture therein, the first member having a formation which defines two opposed walls, and a second member of closed loop form also defining a stoma aperture, the second member having a projection or wall dimensioned and positioned to fit between and resiliently bear against at least one of the walls when the members are connected in such a way as to make sealing engagement with at least the said one wall, characterised in that the first member is of channel formation seen in cross section and has an upstanding tapering rib extending from the base of the channel and between its walls, and in that the second member has a tapering groove, of substantially complementary shape to the rib, in that surface of the projection or wall which faces towards the first member in the mutually coupled condition of the first and second members.

In an embodiment of the invention, each coupling is of resilient synthetic plastics material.

The first member may be secured to the bag and the second member may be secured to the pad or dressing. Alternatively, the first member may be secured to the pad or dressing and the second member to the bag.

In a preferred embodiment of the invention, the aperture is substantially circular and the two opposed walls are substantially annular in form.

The invention will be better understood from the following non-limiting description of an example thereof, given with reference to the accompanying drawings in which.

Figure 1:
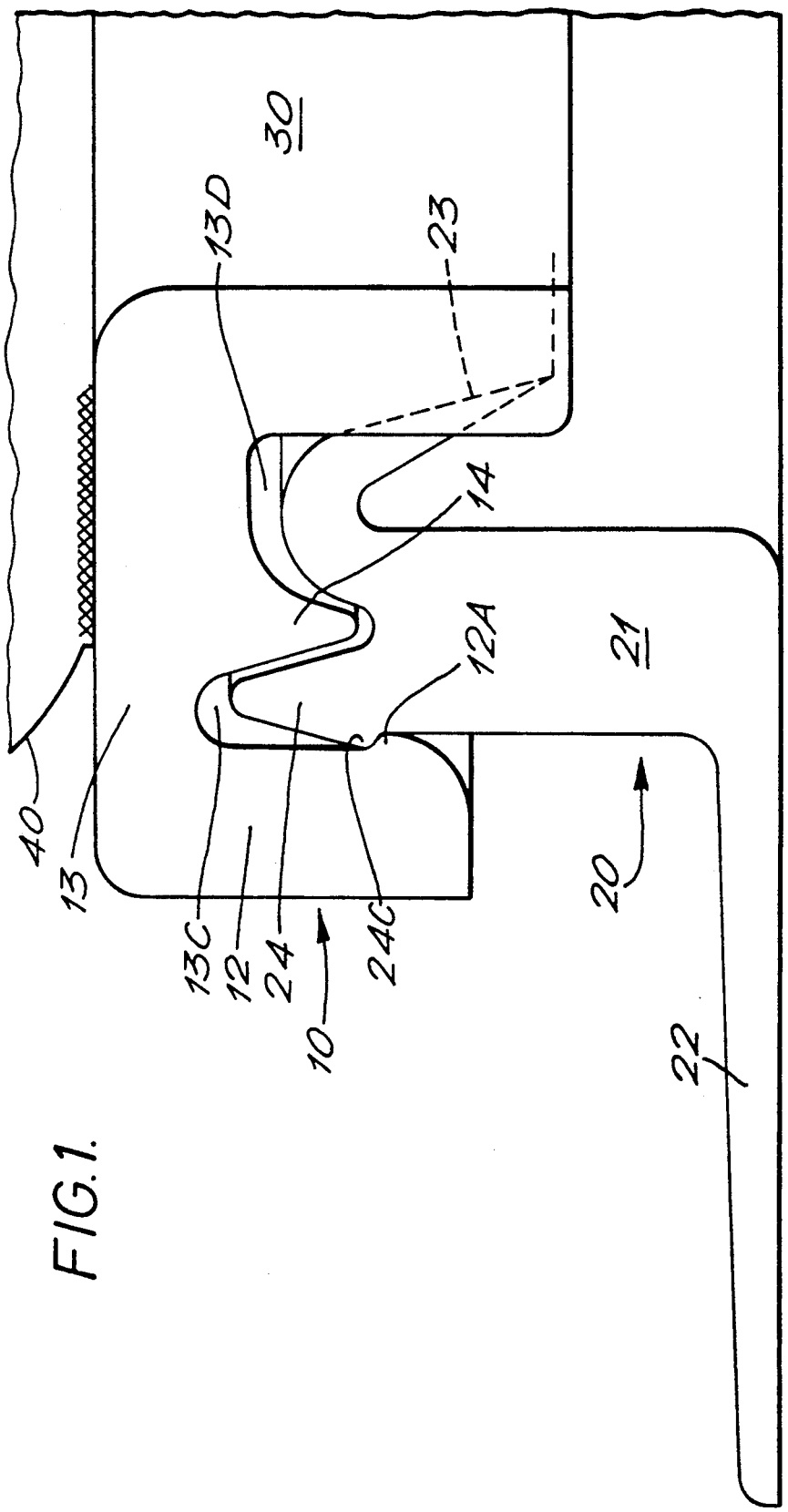
FIG. 1 is a cross-sectional view, taken on a radial plane intersecting the coupling axis, showing part of one example of an ostomy coupling according to the invention with the two coupling members in their mutually coupled condition.

The illustrated ostomy coupling comprises a first member 10 and a second member 20 which, in use, both surround a stomal orifice 30. In the embodiment illustrated, the first member is the bag side member and the second member is the body side member but in an alternative embodiment these may be reversed. A bag 40 is shown secured, e.g. by heat welding, to the first member 10.

The first member 10 is basically in the form of an annular channel having an inner wall 11, an outer wall 12, and a base 13. The ostomy bag 40 is attached in any convenient way to the surface 13A of the base 13. It has been found that when a bag is heat or RF welded as indicated at 42 to the annular channel member 10, the plastics of the member 10 may become affected by the application of energy in that area, resulting in a tendency for the member 10 to be more readily deformed. Hence a tilting of the radially outer portion of the member 10 becomes more likely.

On the opposite side of the base from the surface 13A, there is provided a rib 14 which has tapering surfaces 14A and 14B joined by rounded surface. Taking the depth of the channel as the distance d, the rib extends from the base 13 a distance approximately equal to half the depth d. The wall 14B of the rib merges into a curved wall 13B which forms the base of recess 13C. A rim 12A extends radially inwardly a short distance, from the free end of the wall 12. This rim is conventional and forms no part of the novelty of the invention.

The first coupling member 13 has thereon a grasping tab 13E which may be used to separate the two coupling members when the wearer wishes to manually pull them apart. It also has two ears 13F and 13G which are used if the wearer desires to have the extra security of a belt in which event the ends of the belt would be attached suitably to the respective ears.

Figure 5:
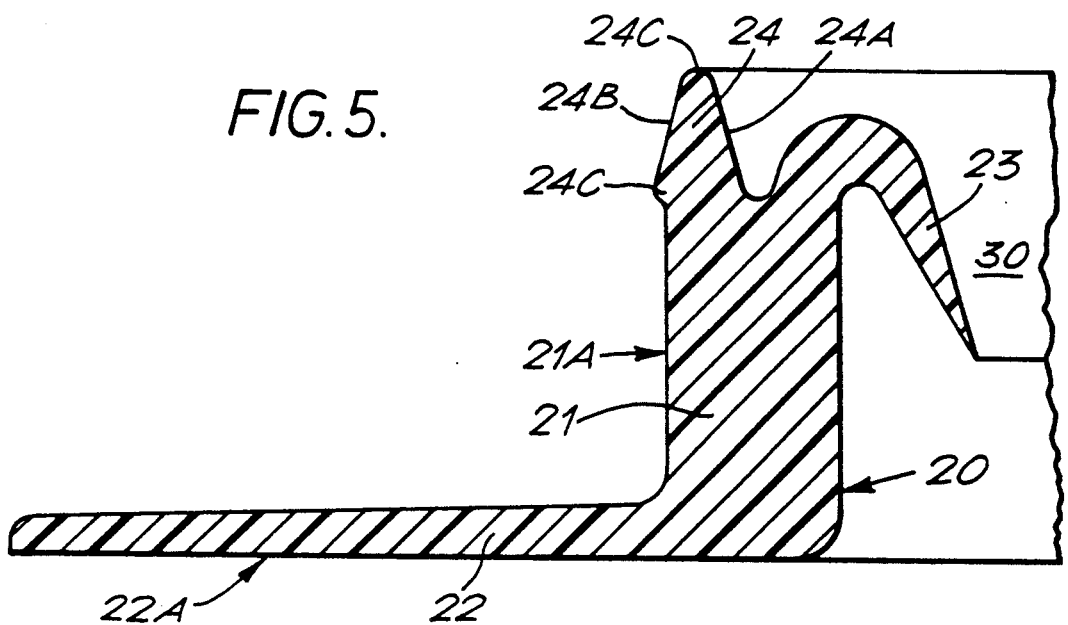
FIGS. 5, 6 and 7 are respectively radial cross-section, front view, and side view of an example of second coupling member according to the invention.
Figure 6:
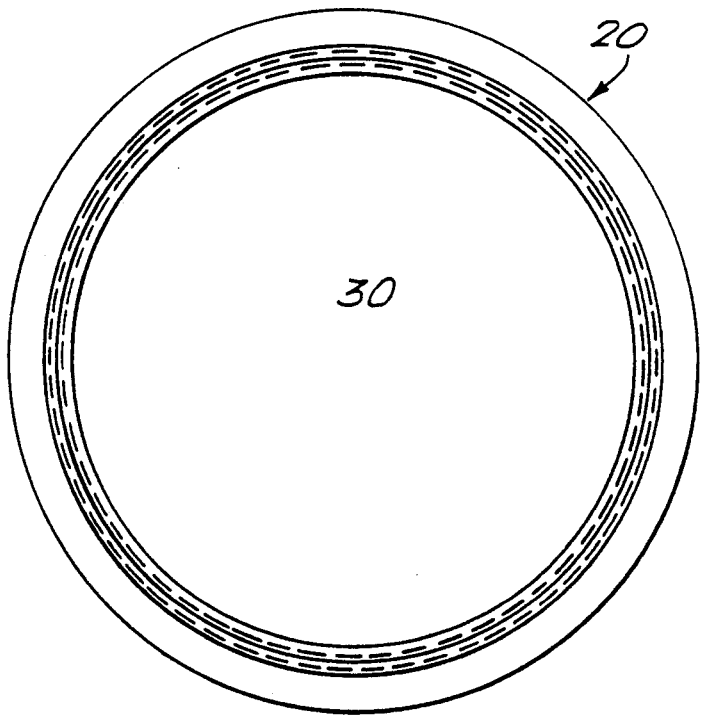
Figure 7:
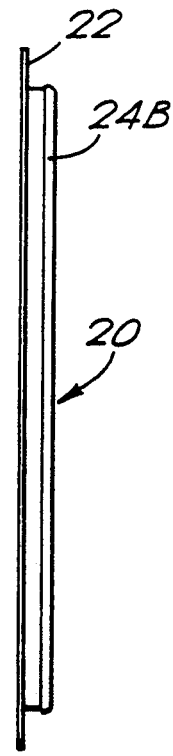

Referring now to FIGS. 5-7, the second member 20 comprises an annular wall 21 made integral with an annular flange 22. A medical grade adhesive pad, not shown, is attached in any suitable way to the surface 22A of the flange 22. The wall 21 and the flange 22 are preferably made integral with each other and the whole member may be moulded from synthetic plastics material. An annular flexible and deflectible sealing strip 23 is integral with and extends from the periphery of the wall 21, in the manner shown. This strip is provided to obtain good sealing between the coupling parts. In this connection, the attention of the reader is drawn to U.K. Patent No. 1 568 860.

Also extending from an end of the wall 21, is an annular rib 24 having tapering surfaces 24A and 24B joined by a rounded surface 24C. The surface 24B terminates in a peripheral rim 24C which stands slightly proud of the external surface 21A of the wall 21. The purpose of the described formations can best be understood by referring to FIG. 1, from which it is seen that the bump 24C co-operates with the rim 12A to hold the two parts together and the seal strip 23 bears against the outer wall 11A of the wall 11. As shown in FIG. 1, the strip 23 is seen dotted in its undeformed position to illustrate the relative dimensions of the parts in the unstressed condition. An ostomy bag 40 is shown attached to the member 10, e.g. by adhesive or by plastics welding. As shown in FIG. 1, the two coupling members are seen slightly separated. In normal use, they will be substantially in contact with one another.

Figure 2:
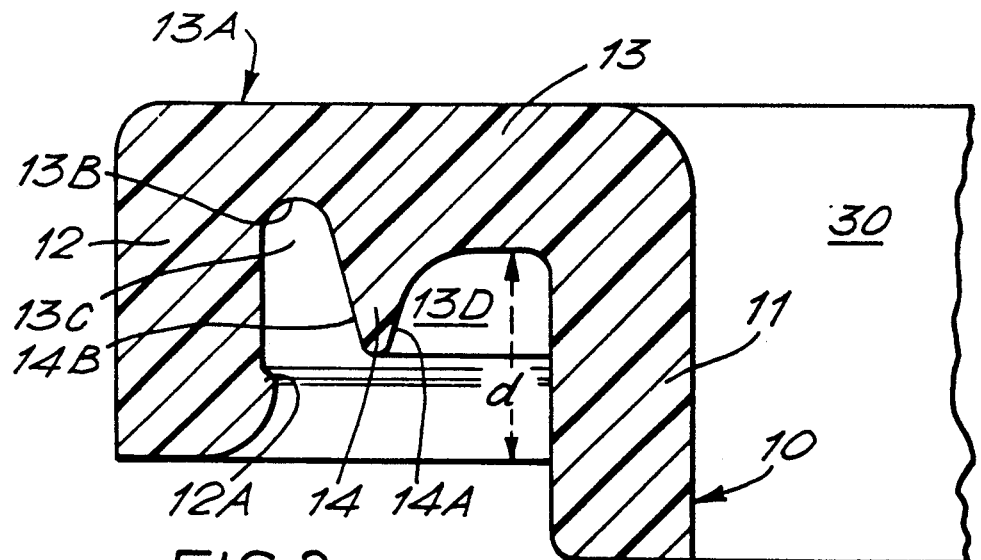
FIGS. 2, 3 and 4 are respectively cross-section, side view and front view of an example of first coupling member according to the invention.
Figures 3, 4:
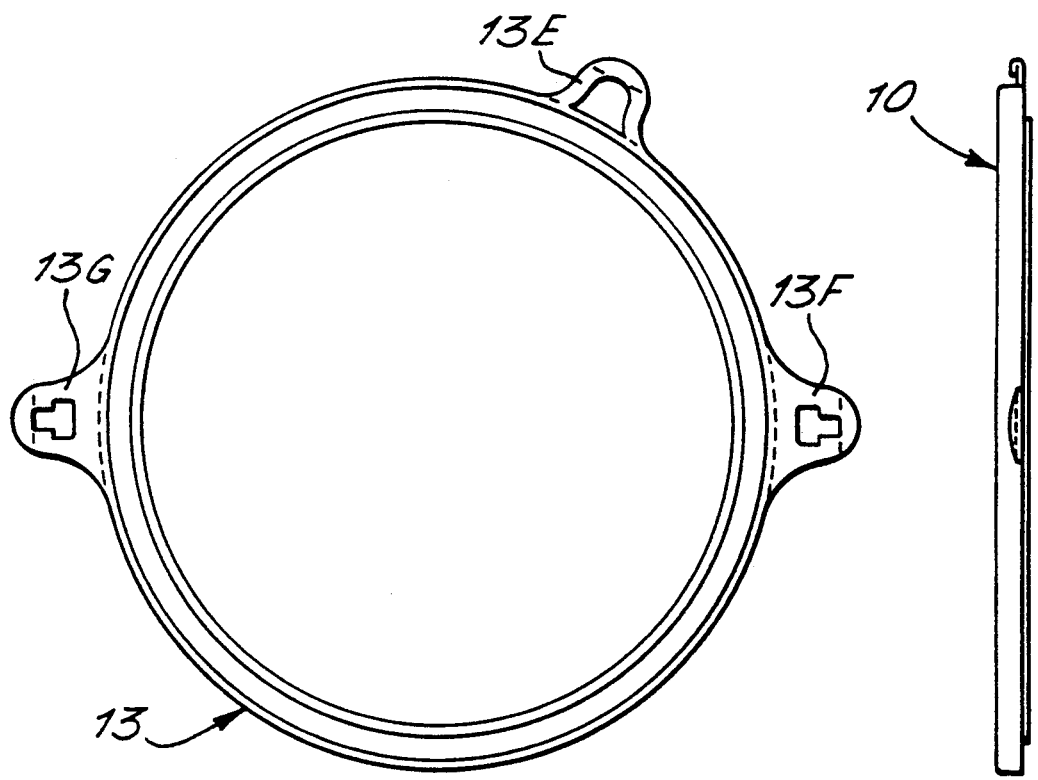

The inter-engagement between the rib 24 and the recess 13C, together with the inter-engagement between the seal strip 23 and the recess 13D (FIG. 2) gives rise to a very secure inter-engagement which is highly resistant to and effectively prevents tilting of one coupling member relative to the other. This prevention of deformation of the member 10 is achieved even in cases where the application of energy in the region 42 has been such that substantial deformation of the member 10 would have been unavoidable in prior art couplings. This advantage of secure inter-engagement is obtained without any increase in the expense or difficulty of manufacture of the parts, and leaves unaffected all the advantageous features of an ostomy coupling of this general type.

Modifications may be made without departing from the invention. For example, as already indicated, the member 10 may be the bag side member and the member 20 may be the body side member. Different specific shapes may be employed for the flexible seal strip 23 and the rib 24. While it is advantageous to have the rounded formation 24C and the peak of the rib 14 rounded, this is not essential and the tapered walls may join at an apex (as seen in cross-section) if desired. Of course the attachment ears 13F and 13G may be dispensed with if desired. Other specific shapes may be employed for the rim 12A.

It will be seen that the particular embodiment disclosed and illustrated herein provides an effective and inexpensive manner of overcoming the problem of undesired tilt in two-part ostomy couplings.

I claim:

1. A coupling for joining a pad or dressing to an ostomy bag comprising:
   a first member with an annular channel surrounding a stomal aperture, said annular channel including two upstanding opposing parallel walls with a base extending between said walls and an upstanding tapering rib extending from said base and between said walls, and
   a second member including an annular wall surrounding a stomal aperture, said annular wall having two diverging extensions, said second member being dimensioned to fit between said opposing parallel walls with each of said extensions bearing against an opposing parallel wall of said annular channel so as to form a sealing engagement of the first and second members, said second member having a tapering groove between said two diverging extensions dimensioned so as to complementary shape to the rib but not expand said diverging extensions when forming said sealing engagement.

2. A coupling according to claim 1 wherein the height of said rib and the depth of said groove are respectively substantially equal to between 40 and 60% of the depth of said channel.

3. A coupling according to claim 1 wherein said rib and groove respectively have surfaces tapering at from 12 to 18 degrees to the axis of the coupling.

4. A coupling according to claim 1 wherein each coupling member is composed of resilient synthetic plastics material.

5. A coupling according to claim 1 wherein said first member is secured to the bag and said second member is secured to the pad or dressing.

6. A coupling according to claim 1 wherein said first member is secured to the pad or dressing and said second member is secured to the bag.

* * * * *